United States Patent [19]
Kronmiller et al.

[11] Patent Number: 5,525,234
[45] Date of Patent: Jun. 11, 1996

[54] METHOD OF IMPROVING THE REVERSE OSMOSIS DEWATERING OF AN AQUEOUS CAFFINE STREAM

[75] Inventors: David L. Kronmiller, Escondido; Craig L. Netwig, Del Mar, both of Calif.

[73] Assignee: King Lee Technologies, San Diego, Calif.

[21] Appl. No.: 182,586

[22] Filed: Jan. 18, 1994

(Under 37 CFR 1.47)

Related U.S. Application Data

[63] Continuation-in-part of Ser. No. 970,167, Nov. 2, 1992, abandoned.

[51] Int. Cl.$^6$ ........................................... B01D 61/04
[52] U.S. Cl. ........................................... 210/639; 210/652
[58] Field of Search ........................................... 210/639, 651, 210/652, 193, 778, 654

[56] References Cited

U.S. PATENT DOCUMENTS 4,203,824  5/1980  Achia et al. ........................... 208/33

FOREIGN PATENT DOCUMENTS 1255268  12/1971  United Kingdom ................... 210/639

Primary Examiner—Frank Spear

[57] ABSTRACT

A process for improving the separation rate of water from a stream of aqueous caffeine and coffee bean extract by reverse osmosis by adding to the stream an effective amount of polyvinylpyrrolidone.

6 Claims, No Drawings

METHOD OF IMPROVING THE REVERSE OSMOSIS DEWATERING OF AN AQUEOUS CAFFINE STREAM

RELATIONSHIP TO OTHER APPLICATIONS

This is a continuation-in-part to our earlier filed application, titled METHOD OF IMPROVING THE REVERSE OSMOSIS DEWATERING OF AN AQUEOUS CAFFEINE STREAM, Ser. No. 07/970,167, filed Nov. 2, 1992, now abandoned.

BACKGROUND OF THE INVENTION

1. Field of the Invention

This invention pertains to the food industry. More particularly, it relates to a method of reducing reverse osmosis membrane fouling and improving reverse osmosis dewatering of an aqueous caffeine stream in the manufacture of coffee and coffee by-products.

2. Description of the Prior Art

In the process of manufacturing coffee, to make the decafinated version, the coffee bean is subjected to various treatments that results in the caffeine being extracted from the bean in an aqueous solution along with various oils and acids. This solution, usually 0.3% caffeine, is then dewatered to produce various concentrates in ranges from 2%, 4% and 6% caffeine and coffee bean extract that are thereafter useful as feed stock in subsequent processes that ultimately result in recovered caffeine used in the chemical industry.

Dewatering is performed using reversed osmosis (RO) units. RO units generally comprise elongated spiral-wound cartridges used either singularly or in groups. The cartridge is commonly constructed of one or more generally rectangular envelopes made of opposed sheets of a proprietary plastic film, sealed about three sides, that passes water molecules thereacross without passing other larger molecules, such as caffeine and other materials, held apart by an interior layer of polysulfone and whose non-sealed edges are separately attached to the sides of an elongated slit formed in the wall of a centralized product tube. The envelope or envelopes are thereafter spiral-wound about the center product tube along with a layer or layers of an open web or stream called "brine channel webbing", to maintain the outer surfaces of a particular envelope free from direct contact with an overlying or underlying layer of membrane envelope, to a tight cylinder about the center product tube.

In use, one end of the spiral-wound cartridge is sealed to prevent water from exiting the layer of webbing and the other end is connected to a source of aqueous caffeine solution. The pressure of the feed solution is raised to exceed the osmotic pressure, the aqueous feed enters into the layer taken up by the brine channel webbing between the rolled envelopes of reversed osmosis material to force the water into the center of the envelopes where it moves by migration and pressure along the layer of polysulfone to enter through the slits into the center product tube and exit the cartridge as clear, fresh water thereby dewatering the aqueous caffeine solution. The feed stream to the cartridge is either referred to as "feed stock" while the filtered water produced from the cartridge is called the "permeate" stream.

Other reverse osmosis units are tubular wound as is well known in the art. Their operation is similar in concept to the spiral-wound units. Reverse osmosis differs dramatically from other forms of separation such as filtration or microfiltration. These latter two processes utilize a paper-like media that have holes formed therethrough to allow passage of water molecules or other molecules that are designed to be removed from the feed stock. To aid separation of the components in filtration and ultrafiltration processes, it is common to complex one or more of the feed stock components to prevent it from passing through the filter. To be successful, it is important to use a stoichiometric quantity of the complexing agent to insure complete complexing of all the component that is to be isolated.

In the reverse osmosis process, the media is a semipermeable membrane that does not have holes like that of the microporous filter media. The feed stock is introduced to the membrane and the pressure raised to a level in excess of the osmotic pressure of the stock to allow water molecules to pass through the membrane into the pure water (permeate) outlet stream.

Presently, the feed stock (approximately 0.3% aqueous caffeine and coffee bean extract solution) is fed to the reverse osmosis (RO) unit under conditions such as 200 pounds per square inch and at a temperature of about 60° Centigrade. Water is drawn off the RO unit as the permeate stream thereby producing a higher concentration of caffeine in the effluent that is the product of the process.

In present-day RO operation, insoluble materials in the feed stock such as silt and colloidal materials such as iron oxide, silicates, such as those of calcium, barium, strontium, magnesium, manganese and other cations react with anions such as sulfates, carbonates, chlorides, etc. and form a foulant or scale on the RO permeable membrane and inhibit the efficiency of the dewatering process. Other foulants found to interfere with the efficiency of the dewatering process are acids such as chlorogenic acid, caffeic acid, quinic acid, citric acid, malic acid, tartaric acid, oxalic acid, pyruvic acid, acetic acid, propionic acid, butyric acid, and valeric acids as well as aldehydes such as acetylaldehyde, propyl aldehyde, butyl aldehyde, and valor aldehyde; ketones such as ketone, didactyl ketone; ketone-alcohols such as acetol, and acetoin, esters such as methyl formate, methyl acetate, methyl propionate, and propyl formate; sulfides such as hydrogen sulfide, dimethyl sulfide, methyl sulfide, mercaptan, thiophene, and cylics such as furan, methyl furan, pyridine, amino acids, amines such as trimethylamine, dimethylamine and ammonia; cellulose both hydrolyzed and non-hydrolyzed; hydrocarbons such as isoprene; unsaturates such as acrolein, caramel, mineral ash, trigonelline and associated processed oils.

Layers of inorganic, organic and other foulant materials, soluble or insoluble in water at varying pH, tend to deposit, after a period of use, on the surface of the semi-permeable membranes and substrates, both supporting and non-supporting. Such deposits seriously impeding the membrane performance by reducing the product flow rate and often the salt rejection rate and thereby impede the processing efficiency. In general, it is believed that if particulate or colloidal matter could be kept suspended, insoluble foulants could be controlled.

Scale-forming type of foulants do not occur if chemical reaction and reaction product precipitation can be prevented. Chemical reaction of the scale-forming reactants can be inhibited and/or controlled by the formation of intermediate products that remain soluble or suspended in the aqueous matrix. Further, precipitation of water soluble material does not occur unless the conditions allowing super-saturation occur.

As the RO unit becomes fouled, the pressure difference between the feed and permeate streams must be raised to maintain adequate flow rates. RO units have a maximum tolerable pressure differential before structural failure is encountered. After this maximum pressure is reached, the process flow rate can only be maintained by shutting down the RO unit and physically cleaning the membranes. This requires draining the feed stock from the unit, filling it with a cleansing solution, cycling the solution through the unit to remove the foulants and scale, draining and rinsing the unit and then recharging the feed stock to the clean unit. Each time this occurs the product stream is interrupted resulting in lost process time, increased labor costs and lost profits.

The prior art has dealt with caffeine in coffee with mixed results. In U.S. Pat. No. 4,160,042, there is disclosed a means of removing caffine from coffee by passing the coffee solution through a bed of ground carob pods so that the caffeine absorbs on the pod material and is removed from the coffee. The carob pods are then lixiviated with hot water to remove the caffeine. This process, however, produces the exact feed stock that the instant invention uses to dewater the caffeine-lixiviated solution.

It is to be noted that this same patent cites a French Patent Application No. 2,231,407 as disclosing the fixing of caffeine on a macromolecular substance in the liquid state and subxequently separating the aggregate so formed by ultra-filtration on a semipermeable membrane. This is a disclosure of mixing a solid with a liquid, to have the solid absorb caffeine from the liquid, then separate the caffeine-complexed solid by filtration. The disclosure also reports that the method has not been accepted for industrial application.

These prior art methods utilize sufficient amounts of macromolecular substances to reach stoichiometric proportions of the caffeine in the feed stock. Such large amounts of material require large equipment to lixiviate the caffeine and then still produce a watered feed stock that requires dewatering before it becomes commercially feasible. This increased the cost of processing the feed stock, prior to dewatering it, constitutes a major impediment in the production of commercial concentrations of caffeine.

SUMMARY OF THE INVENTION

This invention is a surprising discovery that by adding an effective, yet less-than-stoichiometric, amount of a pyrrolidone, such as polyvinylpyrrolidone (PVP), to the aqueous feed stock significantly improves the reverse osmosis dewatering process by inhibiting fouling to the extent that the pressure differential rise throughout the use of the RO unit is significantly reduced thereby allowing the units to remain on line for a longer period of time. The feed stock may be dewatered through reverse osmosis processes without the attendant fouling of the semipermeable membrane and increased pressures that are normally encountered in the dewatering of caffeine-containing stock.

The RO process may be carried on for a longer period of time, at continuously moderate pressures, and with far less fouling of the semipermeable RO membrane, so that down time is curtailed, production costs are minimized, and the final cost significantly reduced over those processes that do not use PVP.

DESCRIPTION OF THE PREFERRED EMBODIMENT

The molecular weight of polyvinylpyrrolidone useful in this invention ranges from a low of the monomer itself, N-vinyl-2-pyrrolidone up to polymerized molecules in the area of 1.6 million molecular weight. The lower molecular weight specie are quite easily soluble while the higher molecular weight are more difficult and resort must be had to alkaline solubilizing solutions. Polyvinylpyrrolidone is produced and marketed in a range of molecular weight, ranging a weight average molecular weight of 10,000 to 1.6 million. The amount of polyvinylpyrrolidone added to the feed stock stream may range from as small as 1 part per million to as high as 400 parts per million. It is not a requirement of this invention that amount of polyvinylpyrrolidone added has any relationship to the stochiometric requirements of the caffeine contained in the feed stock. The Maximum efficacy of polyvinylpyrrolidone in aqueous caffeine feed stock has been found to reside in an area of a weight average molecular weight of approximately 30,000 and a concentration of from about 10 to about 20 parts per million (ppm). The following examples will illustrate the significant aspects of the invention.

EXAMPLE 1

An aqueous solution of polyvinylpyrrolidone of weight average molecular weight 10,000 was injected at 10 ppm into a feed stream of "M Type" coffee bean effluent with a caffeine level of 2%. This was then used as feed to a reverse osmosis system using type AFC 99 tubular polyamide semipermeable membranes used in the process the waste caffeine operating at 200 psi and 60° C. The system was run for twenty hours and then cleaned with 0.5% aqueous solution of surfactant and caustic soda and repeated through five cycles. A 37% increase in flow rate over a similar run without polyvinylpyrrolidone was achieved.

EXAMPLE 2

An aqueous solution of polyvinylpyrrolidone of weight average molecular weight 40,000 was injected at 10 ppm into a feed stream of "M Type" coffee bean effluent with a caffeine level of 2%. This was used as feed to a reverse osmosis system using type AFC 99 tubular polyamide semipermeable membranes in the process the waste caffeine operating at 200 psi and 60° C. The system was run for 20 hours and then cleaned with 0.5% aqueous solution of surfactant and caustic soda and repeated through 5 cycles. A 43% increase in flow rate over a similar run without polyvinylpyrrolidone was achieved.

EXAMPLE 3

An aqueous solution of polyvinylpyrrolidone of weight average molecular weight 630,000 was injected at 10 ppm into a feed stream of "M Type" coffee bean effluent with a caffeine level of 2%. This was used as feed to a reverse osmosis system using type AFC 99 tubular polyamide semipermeable membranes used in the process the waste caffeine operating at 200 psi and 60° C. The system was run for 20 hours and then cleaned with 0.5% aqueous solution of surfactant and caustic soda and repeated through 5 cycles. A 17% increase in flow rate over a similar run without polyvinylpyrrolidone was achieved.

EXAMPLE 4

An aqueous solution of polyvinylpyrrolidone of weight average molecular weight 1,450,000 was injected at 10 ppm into a feed stream of "M Type" coffee bean effluent with a caffeine level of 2%. This was used as feed to a reverse osmosis system using type AFC 99 tubular polyamide semipermeable membranes in the process the waste caffeine operating at 200 psi and 60° C. The system was run for 20 hours and then cleaned with 0.5% aqueous solution of surfactant and caustic soda and repeated through 5 cycles. A 12% increase in flow rate over a similar run without polyvinylpyrrolidone was achieved.

EXAMPLE 5

An aqueous solution of polyvinylpyrrolidone of weight average molecular weight 40,000 was injected at 10 ppm into a feed stream of "M Type" coffee bean effluent with a caffeine level of 4%. This was used as feed to a reverse osmosis system using type AFC 99 tubular polyamide semipermeable membranes in the process the waste caffeine operating at 200 psi and 60° C. The system was run for 20 hours and then cleaned with 0.5% aqueous solution of surfactant and caustic soda and repeated through 5 cycles. A 35% increase in flow rate over a similar run without polyvinylpyrrolidone was achieved.

EXAMPLE 6

An aqueous solution of polyvinylpyrrolidone of weight average molecular weight 29,000 was injected at 12 ppm into a feed stream of "M Type" coffee bean effluent with a caffeine level of 6%. This was then used as feed to a reverse osmosis system using type AFC 99 tubular polyamide semipermeable membranes in the process the waste caffeine operating at 200 psi and 60° C. The system was run for 20 hours and then cleaned with 0.5% aqueous solution of surfactant and caustic soda and repeated through 5 cycles. A 27% increase in flow rate over a similar run without polyvinylpyrrolidone was achieved. Further, the membranes run without polyvinylpyrrolidone fouled irreversibly after 38 hours and test was terminated.

EXAMPLE 7

A commercial caffeine process system consisting of 4 reverse osmosis stages, each containing 40 modules of 18 type AFC 99 tubular polyamide semipermeable membranes per module was used to process caffeine from a decaffeination process using "M type" beans at 6% concentration of caffeine with a process feed temperature of approximately 160° F. and a feed pressure of 250 psi. The polyvinylpyrrolidone, having an average molecular weight distribution of 29,000 to 32,000, was feed at 10 ppm into the process feed water. The process was run for 20 hours with only a 17 psi increase in pressure necessary to maintain flow during the period. The system was then cleaned and another cycle run with the same results. Similar runs without the polyvinylpyrrolidone resulted in fouling of the membranes resulting in excessive pressures, needed to produce the correct flux, necessitating shutdown of the system to prevent damage to the reverse osmosis membranes due to excess pressure.

EXAMPLE 8

A commercial caffeine process system consisting of 4 reverse osmosis stages, each containing 40 modules of 18 type AFC 99 tubular polyamide semipermeable membranes per module was used to process caffeine from a decaffeination process using "M type" beans at 6% concentration of caffeine with a process feed temperature of approximately 160° F. and a feed pressure of 250 psi. The polyvinylpyrrolidone, having an average molecular weight distribution of 29,000 to 32,000, was fed at 10 ppm into the process feed water. The process was run for 20 hours with only a 17 psi increase in pressure necessary to maintain flow during the period. The system was then cleaned and another cycle run with the same results. Similar runs without the polyvinylpyrrolidone resulted in fouling of the membranes resulting in excessive pressures, needed to produce the correct flux, necessitating shutdown of the system to prevent damage to the reverse osmosis membranes due to excess pressure.

EXAMPLE 9

A commercial caffeine process system consisting of 4 reverse osmosis stages, each containing 40 modules of 18 type AFC 99 tubular polyamide semipermeable membranes per module was used to process caffeine from a decaffeination process using "J type" beans at 4% concentration of caffeine with a process feed temperature of approximately 160° F. and a steady state pressure of 210 psi. The polyvinylpyrrolidone, having an average molecular weight distribution of 29,000 to 32,000, was fed at 10 ppm into the process feed water. The process was run for 20 hours with only a 17 psi increase in pressure necessary to maintain flow during the period. The system was then cleaned and another cycle run with the same results.

Similar runs without the polyvinylpyrrolidone required a starting steady state feed pressure of 250 psi, 40 psi higher than with the 10 ppm polyvinylpyrrolidone. Final pressures were 150–200 psi higher than with the polyvinylpyrrolidone and after several cycles lead to excessive pressures causing premature shutdown of the system and irreversible damage to the membranes necessitating replacement of the membranes.

In view of the foregoing then, it is evident that the use of the instant invention has great utility in the Control of fouling in caffeine processing.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the way to achieve substantially the same result are within the scope of this invention.

What is claimed is:

1. A process for improving the reverse osmosis separation rate of water from an aqueous feed stock containing caffeine and coffee bean extract by adding to said feed stock an effective, less-than-stoichiometric, amount of polyvinylpyrrolidone in aqueous solution.

2. The process of claim 1 wherein said polyvinylpyrrolidone has a molecular weight range of from about 10,000 to about 630,000.

3. The process of claim 1 wherein said polyvinylpyrrolidone has a molecular weight of about 30,000.

4. The process of claim 1 wherein said effective amount of polyvinylpyrrolidone ranges from about 1 to about 400 parts per million in the feed stocks.

5. The process of claim 1 wherein said effective amount of polyvinylpyrrolidone ranges from about 10 to about 20 parts per million in the feed stocks.

6. A process for improving the reverse osmosis separation rate of water from an aqueous feed stock containing caffeine and coffee bean extract by adding to said feed stock from about 10 to about 20 parts per million polyvinylpyrrolidone having a molecular weight range of from about 10,000 to about 630,000.

* * * * *